United States Patent [19]

Loyzim

[11] 4,336,858
[45] Jun. 29, 1982

[54] BRAKING SYSTEM FOR A MEDICAL DIAGNOSTIC DEVICE

[75] Inventor: Robert J. Loyzim, Dousman, Wis.
[73] Assignee: General Electric Company, Milwaukee, Wis.
[21] Appl. No.: 957,533
[22] Filed: Nov. 3, 1978
[51] Int. Cl.³ .......................................... B60K 31/00
[52] U.S. Cl. ........................ 180/179; 188/181 C; 246/182 B; 303/109
[58] Field of Search ................... 180/178, 179, 6.28; 324/64, 166, 167, 177; 303/95, 109, 96, 20; 246/182 B; 73/114; 361/242; 188/156, 157, 181 C, 272

[56] References Cited

U.S. PATENT DOCUMENTS

| | | | |
|---|---|---|---|
| 1,593,876 | 7/1926 | Learmont | 180/77 R |
| 2,454,393 | 11/1948 | Leonard | 73/114 |
| 3,496,535 | 2/1970 | Tyzack | 180/178 X |
| 3,542,148 | 11/1970 | Wilson | 180/179 X |
| 3,566,986 | 3/1971 | Udden | 180/79.1 X |
| 3,778,118 | 12/1973 | Podlewski | 303/96 |
| 3,951,226 | 4/1976 | Holmes | 303/99 X |
| 4,084,859 | 4/1978 | Bull et al. | 303/20 |
| 4,170,274 | 10/1979 | Collonia | 303/95 X |

FOREIGN PATENT DOCUMENTS 2139411  2/1973  Fed. Rep. of Germany ...... 180/179

*Primary Examiner*—Joseph F. Peters, Jr.
*Assistant Examiner*—Donald W. Underwood
*Attorney, Agent, or Firm*—Dana F. Bigelow; Douglas E. Stoner

[57] ABSTRACT

A braking system for a mobile medical diagnostic device having forward support wheels operatively associated with proportional electromechanical brakes and a single central steerable wheel assembly at the rear of the device. Means are provided for generating throttle command signals and actual velocity signals and for comparing the two and for applying current to the proportional brakes to a degree which is proportional to the difference in those two signals. When this difference exceeds a predetermined level, a motor brake is further actuated to augment the proportional braking system. Also included is a means for automatically reducing the throttle command signal in proportion to the degree that the steerable wheel assembly is turned from the straight-ahead position.

7 Claims, 9 Drawing Figures

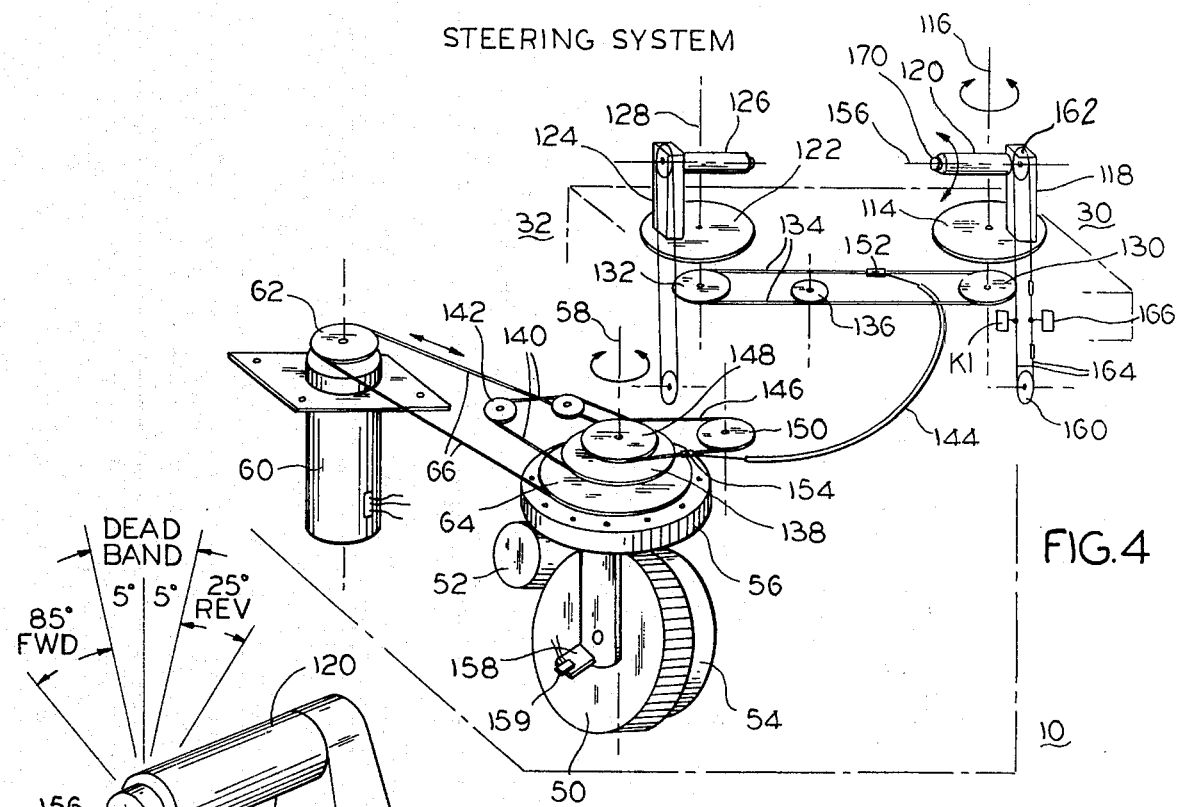
FIG.4
FIG.5
FIG.4a
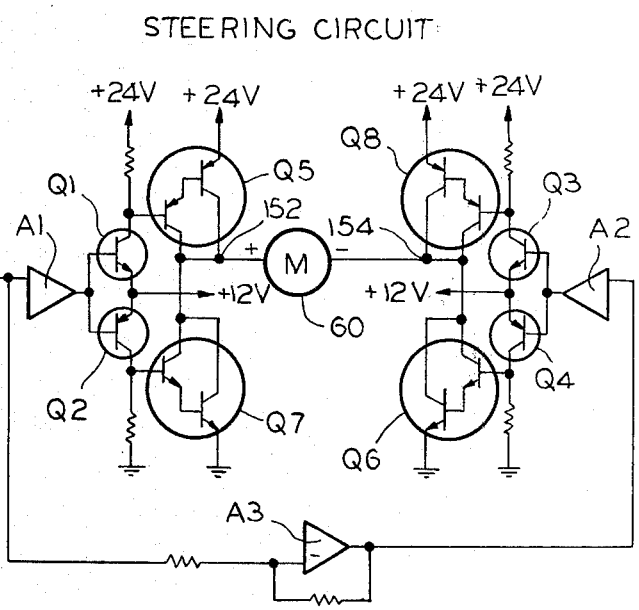
FIG.6

BRAKING SYSTEM FOR A MEDICAL DIAGNOSTIC DEVICE

A stabilization system for a mobile device is claimed in U.S. Pat. No. 4,235,454, issued on Nov. 25, 1980, and assigned to the same assignee as the present invention. A proximity detector system for a mobile device is claimed in U.S. application Ser. No. 957,532, filed Nov. 3, 1978 and assigned to the same assignee as the present invention.

BACKGROUND OF THE INVENTION

The present invention relates generally to a braking system for a device having a self-propelled chassis. More particularly, the invention relates to a an automatic braking system for a medical diagnostic device in which an operator operates the controls while walking behind the device.

Various types of equipment are made mobile by mounting the equipment on a self-propelled chassis. Mobility is particularly significant for medical diagnostic equipment, such as an X-ray device and a scintillation camera device for obtaining diagnostic images of a patient. In many cases, the patient requires intensive care or critical care and cannot be moved, so the diagnostic device must be transported to the patient. The device may be required to be operated virtually anywhere in the hospital. The device must maneuver along extremely long corridors, around life support systems and around monitoring systems or traction devices. The device must also move in and out of elevators, through doorways, up wheelchair ramps, over carpeting and tile, and across small open thresholds.

A problem is presented by the mobilization of scintillation camera equipment which is used to detect gamma rays photons emitted from a body in which a radioisotope has been infused to produce a diagnostic image of the patient. Scintillations occur where photons are absorbed by crystalline material. The scintillations are received by a detector head which contains scintillation crystals, photomultiplier tubes and lead shielding. A typical system is based on the camera of Anger, as disclosed in U.S. Pat. No. 3,011,057, and is herein incorporated by reference. The detector head, along with the suspension arm, weighs approximately 300 pounds. The suspension system and column for the detector head add more weight along with the very high density of electronic instrumentation used to analyze and display the diagnostic images of the patient. The substantial size and weight of the diagnostic equipment requires a similarly substantial chassis and mobility drive system to transport the equipment. The combined equipment and mobility chassis weighs over 2,000 pounds and presents the problem of safely maneuvering, steering and braking the device while it is being moved and then stabilizing the device once it is in position.

Typical mobility chassis of the prior art use conventional four-wheeled systems with mechanical steering and braking systems. A particular problem with mobility devices is in the application of the braking systems. Typical devices of the prior art relied upon the natural friction of the system to stop the devices once power was reduced to the propelling system. A brake was either "on" or "off" and was utilized primarily as a parking brake or as an emergency brake in critical situations.

Accordingly, one object of the present invention is to provide a diagnostic device which can be safely operated at relatively high speeds through corridors and can be slowly maneuvered into tight locations.

Another object is to provide a diagnostic device which can be easily controlled by an operator walking behind the device.

Still a further object of the present invention is to provide a diagnostic device having a steering system which can be readily operated with either hand to control direction, velocity, steering and braking for the device.

SUMMARY OF THE INVENTION

The invention is directed to a braking system for a mobile medical diagnostic device, such as scintillation camera equipment, which must be quickly and safely maneuvered within a hospital. In the scintillation camera example, the chassis for the device includes two forward support wheels operatively associated with proportional electromechanical brakes and a single central steerable wheel assembly at the rear of the device. The brakes are engaged proportionally in response to the electrical current applied to the system. The central rear wheel is also the drive wheel having a bidirectional variable speed electric motor adapted as a means for self-propelling the device. The device is controlled by at least one handle assembly located approximately waist high at the rear of the device and readily responds to wrist action of an operator walking behind the device. The system includes circuitry for sensing the left and right positions of the handle assembly and for actuating an electric motor coupled to the steerable wheel assembly to direct the wheel assembly into a position corresponding to the position of the handle assembly. The handle assembly also includes a throttle hand grip which is independently rotatable about its longitudinal axis. The hand grip is connected to circuitry for controlling the forward and rearward directions and the velocity of the device.

The brakes are automatically applied in proportion to the difference between the actual speed and the desired speed as indicated by the throttle. The system includes a means for sensing the present velocity of the device and producing a present velocity signal. A means is provided for sensing the position of the throttle and producing a throttle command signal. Circuitry means are provided for comparing the present velocity signal to the throttle command signal, and when the velocity signal is greater than the throttle command signal applying current to the brakes proportionally to the difference in the signals.

BRIEF DESCRIPTION OF THE DRAWINGS

While the novel features of the invention are set forth with particularity in the appended claims, the invention will be understood along with other features thereof from the following detailed description taken in conjunction with the drawings in which:

FIG. 4 is a cutaway perspective view showing the mechanical elements of the steering system;

FIG. 4a is an enlarged view of the tachometer shown in FIG. 4;

FIG. 5 is an enlarged view of the right handle assembly shown in FIG. 4;

FIG. 6 is a schematic diagram of the circuitry for the steering system;

DETAILED DESCRIPTION OF THE DRAWINGS

Figure 1:
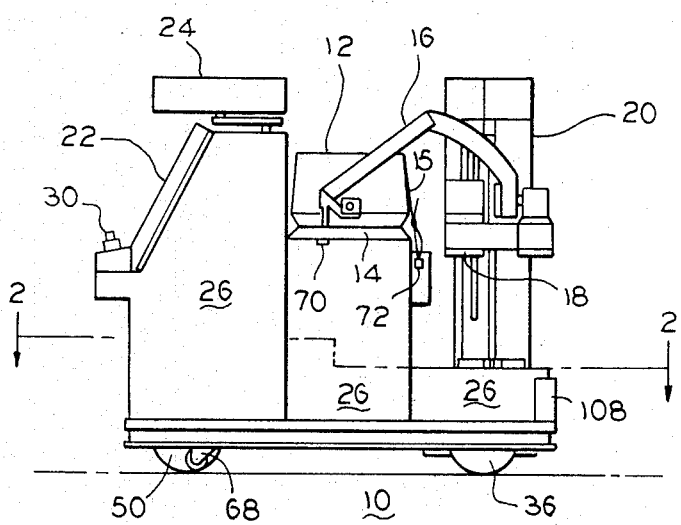
FIG. 1 is a side elevation view of a mobile scintillation camera device incorporating the invention.

Referring first to FIG. 1, there is shown a mobile scintillation camera device 10 in position for being moved within a hospital. The detector head 12 contains the scintillation crystals, photomultiplier tubes and lead shielding for receiving gamma ray energy. During analysis, the detector head 12 is positioned over the patient; however, the detector head is shown in the transportable position resting on a support pad 14 and secured by a hold down strap 15. The detector head 12 is supported by a suspended arm 16 cantilevered from a suspension system indicated by numeral 18. The suspension system 18 is contained within a vertical column structure 20 and controls the vertical position of the detector head 12 at desired positions along the vertical column structure. A control console 22 contains camera electronics, imaging oscilloscopes, and controls for accessory equipment for data analysis. The diagnostic image from the patient is normally displayed at persistance oscilloscope 24. Enclosed within housings 26 (but not shown) are a counterpoise and rotation system for column 20, the storage batteries for providing d.c. power, and all of the electronics and circuitry for the equipment and mobility for the device. The device 10 utilizes conventional 115 volt a.c. power for detection, imaging and data processing during analysis of the patient and utilizes the storage batteries for d.c. power for the mobility systems used to maneuver the device to desired locations within the hospital. The mobility controls are located approximately waist high at the rear of the device. The controls include a right handle assembly 30 and a left handle assembly 32 which are synchronized so that the device can be controlled by either or both hands of the operator.

Figure 2:
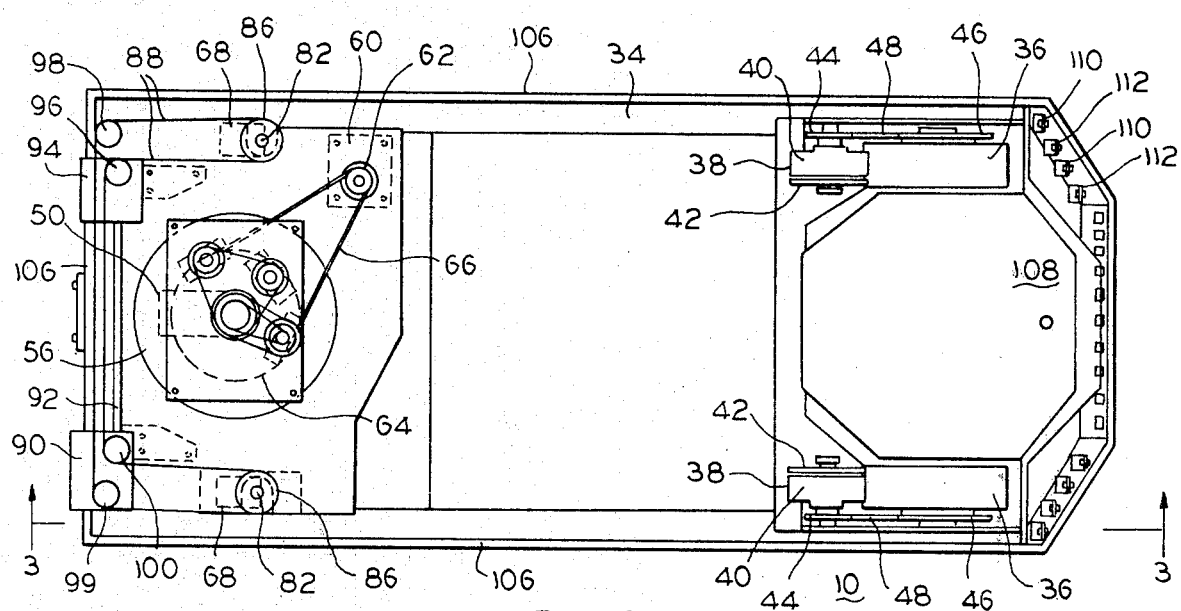
FIG. 2 is a sectional view of the chassis of the device taken along line 2—2 of FIG. 1.
Figure 3:
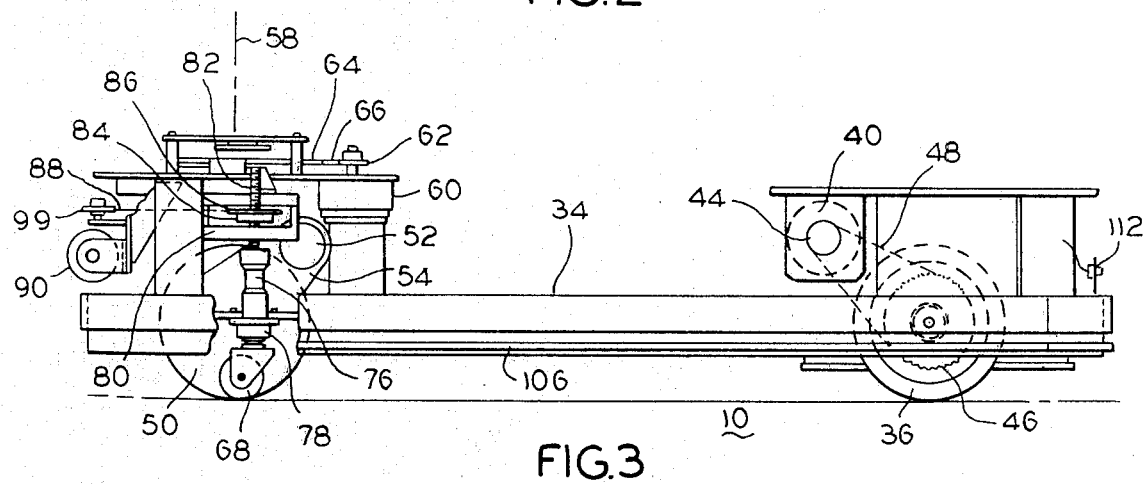
FIG. 3 is a sectional view of the chassis system taken along line 3—3 of FIG. 2.

Referring now to FIGS. 2 and 3, there are shown the features of the chassis mobility systems. The mobility systems are supported by and attached to a rectangular frame 34 surrounding the device 10. The front of the device is supported by two wheel assemblies 36 attached by conventional bearing housings to frame 34. The primary braking system for the device is provided by proportional electromechanical brakes 38. A suitable brake is available from SIMPLATROL corporation under part number B-133. The brakes 38 utilize an electromagnetic coil within a housing 40 and an engageable magnetic disc 42 having an abrasive surface. The amount of engagement by the disc 42 and housing 40 is proportional to the amount of current applied to the electromagnetic coil. The brakes 38 are connected by brake sprockets 44 to wheel sprockets 46 by a continuous chain 48.

The rear of the device 10 is supported by a central, steerable wheel assembly 50. The three-wheeled mobility system permits the device to be extremely maneuverable. In this example, the central wheel assembly 50 is also the drive wheel having means for self-propelling the device 10. The self-propelling means is provided by a bi-directional variable speed motor 52 coupled to the wheel assembly 50 by a conventional gear drive 54. The wheel assembly and self-propelling means are mounted to a rotatable bearing platform 56 having a vertical axis of rotation 58 and mounted to frame 34. The steerable wheel assembly 50 is coupled to a bidirectional steering motor 60 by a steering drive sprocket 62 and a steering wheel sprocket 64 connected by a continuous chain 66.

Several features of the device are described having sprocket and chain drive systems. It should be understood that various gear trains or belt drive systems could be employed in alternative embodiments.

The system includes circuitry which will be described later in detail such that the handle assemblies 30 and 32 control the steering motor 60 which controls the left or right direction of device 10; and control the motor 52 which controls the forward or rearward direction and velocity of the device.

The three-wheeled mobility system provides a very compact and maneuverable system for controlling and transporting the device. However, when the scintillation camera is positioned for analysis and the heavy detector head 12 is extended to the side of the device over the patient, the three-wheeled mobility system does not provide a stable support for the device. In order to provide a more stable support for the device during diagnostic analysis, a stabilization system is provided having extendable casters 68 near the rear corners of the device. The stabilization system is automatically actuated when an a.c. power cord of the device 10 is plugged into a wall outlet and the detector head 12 is lifted from the support pad 14. A magnetic tape switch 70 is provided under support pad 14 and a sensing microswitch 72 is provided at the end of the detector head hold down strap 15 (as shown in FIG. 1) which must both be closed to indicate that the detector head is lifted from the support pad in order to actuate the system. The casters 68 have vertical shafts 76 which are slideable through bearing journals 78 attached to frame 34. Each caster drive assembly 80 includes a lead screw 82 driven by a confined rotatable nut 84, which is rotated clockwise or counterclockwise by a sprocket 86 and a continuous chain 88. The stabilization system is operated by a bidirectional, split-phase stabilization motor 90 having an output shaft 92 coupled to a gear box 94. The gear box 94 has a drive gear sprocket 96 coupled to the continuous chain 88. Idler sprockets 98, 99 and 100 are provided to synchronize the two caster drive assemblies to the drive gear sprocket 96. During operation, when the device is plugged into a wall outlet and the detector head is lifted from the support pad, circuity is provided such that stabilization motor 90 will automatically operate to drive gear sprocket 96 and rotate the continuous chain 88 thereby rotating the confined nuts 84 which drive the lead screws downward and extend casters 68 until a lower limit switch is actuated. At this time the central steerable wheel assembly is raised from the floor and the device is supported by the two front wheels 36 and the two rear stabilizing casters 68. Similarly, when the detector head is placed on the support pad and the hold down strap 74 is secured, the circuitry will again activate the motor 90 in the opposite direction whereby the casters will be retracted until an upper limit switch has been actuated and the stabilization system will again come to rest.

Safety is of the uppermost importance when the device is being moved. If the operator should suddenly release the handle assemblies, 30 and 32, the controls will immediately return to a neutral position and the brake system 38 will automatically be applied. A touch sensitive tape 106 extends along the rear and sides of the device. If the tape comes in contact with an obstacle, it deactivates the drive motor 52 and automatically applies the brakes. Another unique safety feature of the device is a proximity detector system 108 which detects any obstacles within twelve inches to the front of the device and automatically applies the brakes which stop the device before reaching the obstacle. The proximity detector system 108 is an ultrasonic transmitter/receiver which incorporates 27 acoustic transducers arranged above the front bumper of the device. Thirteen of the transducers are dedicated to transmitting and are identified by numeral 110, and 14 of the transducers are dedicated to receiving the reflected signal and are identified by numeral 112. If there are no obstacles within 12 inches of the front bumper, there will be no reflected signal, but as an obstacle moves into the field, the amplitude of the reflected signal increases and a "brake command" signal is produced.

As shown particularly in FIGS. 4, 5 and 6, the steering system can be fully described. The steering system is controlled by a pair of adjacent synchronized handle assemblies located at the rear of the device as previously discussed. The right handle assembly 30 has a rotatable base 114 with a generally vertical operative axis 116. The handle assembly and operative axis are tilted slightly to the rear to facilitate manipulation by the operator. A support 118 extends upward from base 114 and supports a hand engagable grip 120 which extends generally horizontally from the support and through the operative axis 116. Similarly, the left handle assembly 32 has a rotatable base 122 and a support 124 having a hand engagable grip 126 extending generally horizontally through an operative axis 128. Handle assembly 30 and handle assembly 32 are interconnected so that a rotation of either handle assembly will produce a synchronized movement by the other handle assembly. The synchronized handle feature provides an excellent feel of the controls for the operator. When the operator grips both handle assemblies, the wrist action used to steer the device tends to position the body of the operator in the proper position for trailing the device. The synchronized handle assembly feature also permits the device to be steered with either or both hands by the operator. The handles are synchronized by a sprocket 130 attached to base 114 and concentric about axis 116, and a sprocket 132 attached to base 122 and concentric about axis 128 interconnected by a continuous chain 134. Chain 134 also couples the handle assemblies to a potentiometer 136 whose wiper arm voltage varies in proportion to the direction and amount of rotation of the steering handles. Wheel assembly 50 includes a sprocket 138 which is concentric with axis of rotation 58 and coupled by a continuous chain 140 to another potentiometer 142. The wiper arm voltage of potentiometer 142 varies with the direction and amount of rotation of the drive wheel assembly. The difference in these wiper arm voltages of potentiometers 136 and 142 is used to control the steering motor 60. The handle assemblies are normally in the lateral position for going straight and are rotatable to a maximum turning position of 70° to the right or left of the lateral position.

If the steering handle assemblies were to be turned rapidly in either direction, a slight lag would be presented until the circuitry and steering motor 60 could rotate the wheel assembly 50 corresponding to the position of the handles. Such a lag could result in oversteering or excessive corrective steering by the operator. To limit this response lag, the steering handle assemblies are mechanically linked to the drive wheel assembly so that the position of the handle assemblies closely corresponds with the relative position of the wheel assembly. A centrally biased, push-pull cable 144 is interconnected between chain 134 of the handle assemblies 30 and a chain 146 coupled to the drive wheel assembly 50 by a concentric sprocket 148 and an Idler sprocket 150. The cable ends 152 and 154 are spring-loaded to allow a maximum of 15° offset in the steering handles from the drive wheel assembly. The mechanical link 144 will prevent any further steering handle movement until the drive wheel assembly catches up within the 15°. This arrangement gives the operator a better feel for the controls and prevents oversteering.

Referring particularly to the schematic diagram of FIG. 6, the steering system circuitry will be described. Voltage tapped from potentiometers 136 and 142 is applied to a differential amplifier A0 having an output of the analog difference between the two input commands. This signal is then applied to two operational amplifiers A1 and A2 which produce amplified signals in proportion to the differences between the two voltages. The amplifier A1 is connected to transistors Q1 and Q2. An inverter A3 inverts the signal and applies it to the other amplifier A2 which is connected to transistors Q3 and Q4. Transistors Q1, Q2, Q3 and Q4 act as proportional switches enabling or disabling portions of the circuit. For example, when the handle assemblies are turned to the right, the differential input voltage is positive and A1 causes Q1 to conduct in proportion to the magnitude of the voltage. The signal from Q1 causes a Darlington pair Q5 to conduct a proportional amount making the input 152 to the steering motor 60 more positive with respect to ground. Similarly, inverter A3 inverts the proportional signal and amplifier A2 causes Q4 to conduct in proportion to the voltage. The signal from Q4 causes Darlington pair Q6 to conduct, bringing the other side 154 to motor 60 closer to ground potential, resulting in voltage across the motor and a clockwise rotation. The rotation of steering motor 60 causes the chain 140 to rotate potentiometer 142 until the wiper arm voltage equals that of potentiometer 136. When the wiper arm voltages of potentiometers 136 and 142 are equal, there is no differential signal to amplifiers A2 and A3 and the motor 60 rests with wheel assembly 52 positioned corresponding to the position of the handle assemblies. In a similar manner, when the handle assemblies are turned to the left, the differential input voltage is negative, the amplifier A1 produces signals with Q2 and Q7 and amplifier A2 produces signals with Q3 and Q8 to produce a proportional counterclockwise rotation of a steering motor 60.

Figure 7:
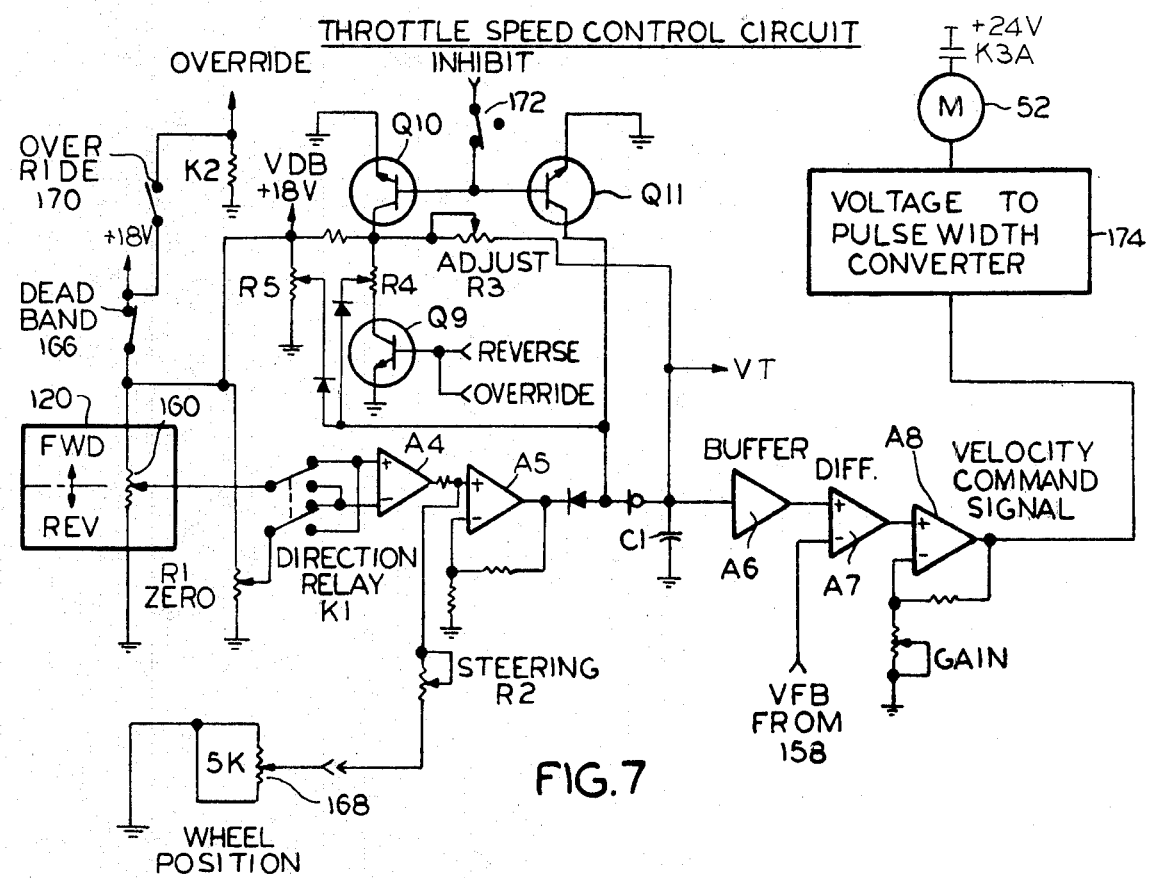
FIG. 7 is a schematic diagram of throttle circitry for the steering system.
Figure 8:
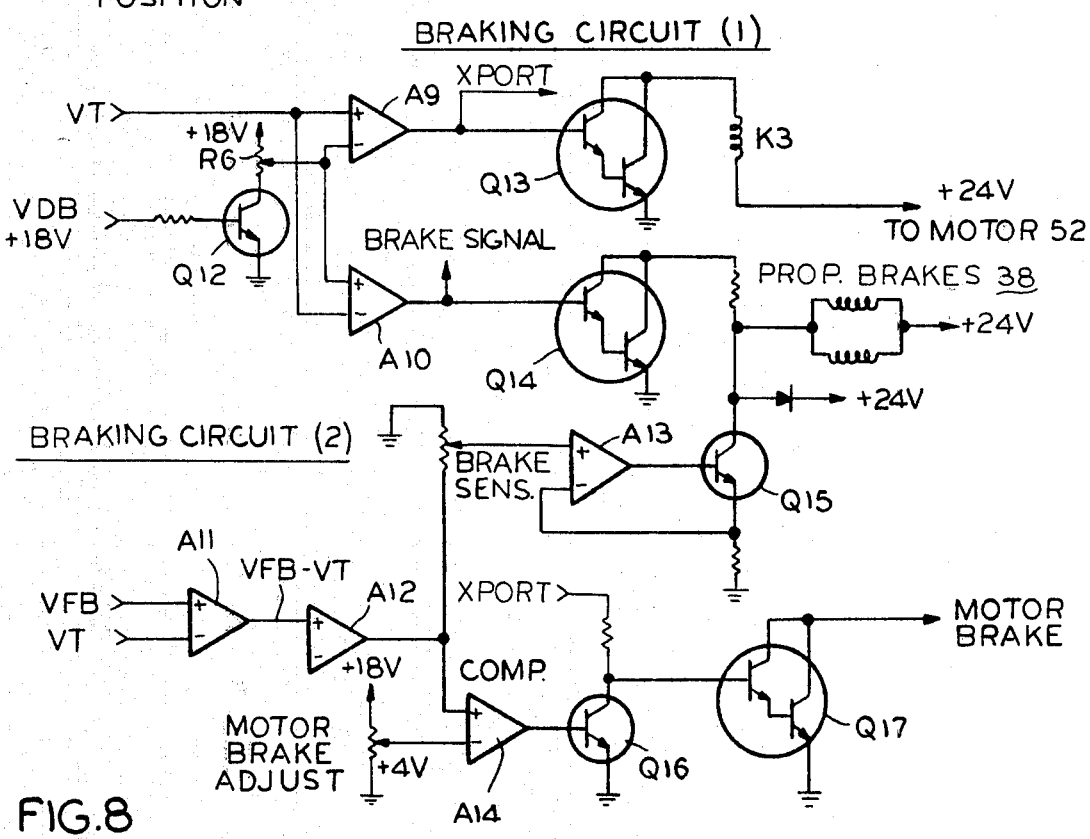
FIG. 8 is a schematic diagram of the braking circuity for the device.

Referring to FIGS. 4, 5 and 7, the throttle speed control is described. The throttle control is described in terms of right handle assembly 30; however, it should be realized that the throttle control could be adapted to left handle assembly 32 and preferably both handles could be synchronized so that either handle could be used to control the speed of the device. A forward or rearward direction signal and a throttle command signal is actuated by hand engagable grip 120 which is rotatable about its longitudinal axis 156. The hand grip includes means for centrally biasing the rotation of the hand grip to a neutral position, such as is a dual acting torsional spring (not shown). The electric circuitry of the system senses the direction and amount of rotation of grip 120 and produces a throttle signal proportional to the amount of rotation so that the self-propelling means of motor 52 is responsive to the throttle signal to control the velocity of the device. When the upper surface of hand grip 120 is rotated in a forwardly direction, the throttle signal is produced to propel the device forward, and when rotated in the rearwardly direction, produces the throttle signal to propel the device rearward. The throttle signal is a proportional voltage obtained from hand grip 120 and is modified by two other signals. The first signal modifies the throttle signal voltage to slow down the device while making turns, and the second signal decreases the throttle signal voltage while in reverse. The resulting modified voltage is called the throttle command signal and is labled VT. This voltage is compared with the present velocity signal of the device, called VFB, and, if the present velocity signal VFB is slower than the throttle command signal VT, the comparator sends out a positive velocity command signal to a voltage-to-pulse-width-converter which speeds up the propelling motor 52. If the throttle command signal VT is less than the present velocity signal, no velocity command signal is produced and the motor naturally slows down. The present velocity signal VFB of the device is obtained by an electromechanical tachometer 158 having a shaft idler 159 which rides against the wheel of the wheel assembly 50 and produces a signal proportional to the velocity of the device which signals pass along leads 161.

If a dangerous condition is detected, an "inhibit" line is activated and VT is pulled to ground, dropping the throttle command signal to zero and stopping the device. In general terms, the velocity command signal is produced by comparing the throttle signal to the present velocity signal of the device and amplifying the difference. This voltage difference is the velocity command signal and is fed to the propelling motor 52 to correct the motor speed, producing a velocity in direct proportion to the velocity command signal. The input to the throttle speed control circuit is the throttle potentiometer 160 which is spring-loaded to the center position and coupled to hand grip 120 by a sprocket 162 and a continuous chain 164. A "dead-band" switch 166 is also coupled to continuous chain 164 and turns on power to the throttle input circuit only when the hand grip is rotated five degrees past the center position. This five degree swing is incorporated to prevent the device from being moved by any accidental, slight movement of the hand grip. After the throttle is moved past the five degree "dead-band" portion, power is applied to the input circuit. The voltage on the wiper arm of the throttle potentiometer 160 is directly proportional to how far the throttle is rotated. This proportional voltage is applied through a directional relay K1 to an operational amplifier A4. In amplifier A4, the throttle voltage is subtracted from a "zero" reference voltage and adjusted by R1 to obtain an output of zero when the spring loaded hand grip is in the center rest position. Any hand grip movement past the five degree "deadband" produces a positive, proportional voltage at the output of A4. The directional relay K1 switches the inputs of A4 when the device is operated in reverse so that moving the hand grip 120 in the rearward direction still produces a positive voltage at the output of A4. The output of A4 is also controlled by the amount of steering of the wheel assembly 50. A 5K potentiometer 168 is also coupled to the wheel assembly by continuous belt 140, and is varied in proportion to the amount that the wheel assembly is rotated in the steered position. The wiper arm of potentiometer 168 is tied through a steering reduction potentiometer R2 to the output of amplifier A4. When the wheel assembly 50 is not rotated, there will be no attenuation of the output of A4. As the amount of rotation of the wheel assembly is increased, this varies the signal from potentiometer 168 and decreases the output signal of A4. During maximum turning, the output of A4 is decreased by ½ the signal created with no turning. The modified output of A4 is amplified by a gain stage at an amplifier A5, whose output clamps a supply voltage VDB in proportion to the amount of the hand grip movement, resulting in throttle command signal VT. When the dead band switch 166 closes, the supply voltage of 18 volts is connected to the input circuit. This supply voltage VDB is connected through an acceleration adjust potentiometer R3 to the output of A5, where it is clamped in proportion to the movement of the hand grip. When the hand grip is advanced, the output of A5 increases, causing less VDB clamping, which results in a larger VT voltage. When the throttle position is reduced, the output of A5 decreases, causing more VDB clamping, which results in a smaller VT voltage. The VT voltage has an upper limit controlled by a low speed potentiometer R4 and a forward speed potentiometer R5. With the hand grip in the forward position, a "reverse" signal is zero and a transistor Q9 disconnects the low speed potentiometer R4 from the circuit. The forward speed potentiometer R5 is adjusted to produce a maximum 15.7 volt VT signal when the hand grip is fully advanced, which corresponds to a maximum forward speed of three feet per second. When the hand grip switches the directional relay K1 to the reverse direction, the reverse signal goes high, turning on Q9 which connects the low speed potentiometer R4 into the circuit. Potentiometer R4 is adjusted to produce a maximum 4.1 volt VT signal when the throttle is fully advanced in the reverse position, effectively overriding the maximum forward speed potentiometer R5. A 4.1 volt VT signal produces a maximum speed of 0.6 feet per second.

The VT signal is controlled by one other circuit. This circuit consists of transistors Q10 and Q11, normally turned off. The bases of the transistors are tied to a common point called the "inhibit" line. Whenever an "inhibit" line signal goes high, such as an interruption of the touch sensitive tape 106 or the proximity detectors 108, these transistors turn on and ground signals VDB and VT, respectively. Grounding these signals will stop the motor 52 and will apply brakes to stop the device as will be described later. However, an override button 170, located at the end of hand grip 120 to energize a relay K2 and switch 172 opens, disconnecting the inhibit line from the circuit. Pushing the override button 170 also generates an "override" signal that turns on the transistor Q9, reducing the maximum speed in the override condition to the 0.6 feet per second velocity. This allows the device to be maneuvered into tight locations at a safe reduced speed, even though the touch tape is contacted or obstacles are within 12 inches of the device.

The combined resulting throttle command signal VT charges up capacitor C1. The acceleration of the device is determined by the time constant of capacitor C1 and the adjustment of potentiometer R3. The signal VT is then applied to a buffer stage A6. The output of the buffer stage A6 is applied to a differential stage A7, along with signal VFB. As previously described, VFB is a voltage signal from tachometer 158 and is proportional to the motor speed. The output of the differential stage A7 is the voltage difference VT-VFB. If the hand grip is generating a command signal calling for the device to move faster than the motor is presently moving, the output from the differential stage A7 will be a positive voltage which becomes amplified by amplifier A8 and is fed to a voltage-to-pulse-width-converter 174, which in turn speeds up the motor 52. If, however, the throttle's command signal calls for a speed lower than the present motor speed, the output will be zero, effectively turning off the propelling motor. This procedure is constantly taking place, comparing the throttle command signal VT with the present velocity signal VFB and correcting the motor speed so that the device velocity is in direct proportion to the throttle signal at hand grip 120.

Referring to FIGS. 2, 3, 5 and 8, the brake system is fully described. As previously discussed, the primary braking system for the device is provided by proportional electromechanical brakes 38 operatively associated with wheel assemblies 36. The amount of engagement of the brakes is proportional to the amount of current applied to the electromagnetic coil. An additional independent brake is located at the shaft of the propelling motor 52. This secondary brake acts as an emergency or motor brake system for the device. The brake signals for the two independent brakes are developed by two circuits. Braking circuit (1) monitors the throttle command signal VT, and energizes a relay K3 when the signal is detected and applies power to propelling motor 52. If the throttle is returned to the neutral position, this circuit will de-energize K3 and also apply a low voltage to the proportional brakes 38 and will act as an automatic parking brake. Braking circuit (2) compares the present velocity signal VFB to the throttle command signal VT and activates both the proportional brakes and the motor brake if the throttle command signal calls for a lower speed. The circuit will also disconnect the brakes if the throttle command signal calls for an increase in the speed of the propelling motor. The throttle command signal VT is utilized as the input to both circuits. VT is generated by the position of the rotatable hand grip 120 as previously discussed. The VT signal is applied to the positive input of an operational amplifier A9, and to the negative input of another operational amplifier A10. A reference voltage is connected to the negative input of A9 and to the positive input of A10 through a resistor R6. A transistor Q12 is in series with the reference voltage and when Q12 turns on, the reference voltage decreases in value. When the hand grip is advanced past the 5° "dead-band", the VT signal becomes greater than 1.0 volts and the VDB signal becomes positive, turning on Q12, which lowers the reference voltage to A9 and A10. This will cause a positive output voltage from A9 which turns on a Darlington pair Q13. The Darlington pair Q13 conducts, which energizes K3 and applies power to propelling motor 52. Also, the output from A10 will drop to zero, turning off a Darlington pair Q14 and de-energizing the proportional brakes 38. When the hand grip 120 is returned to the neutral position, the VT signal goes to zero and VDB goes to zero, turning off Q12 and increasing the reference voltage. This will cause the output of A9 to be zero, turning off Q13 and de-energizing K3. With K3 deenergized, there is no power to the propelling motor 52. The output of A10, referred to as the "brake signal", will go high, turning on Q14. This applies partial power to proportional brakes 38 after the device stops.

Braking circuit (2) uses the throttle command signal VT and the present velocity signal VFB as inputs. These signals drive a differential amplifier A11, whose output is high only when the present velocity signal VFB is greater than the throttle command signal VT. This output is amplified at A12 which has the amplified VFB-VT voltage applied to the positive input of amplifier A13. When the voltage from A13 is high, a transistor Q15 turns on, applying power to the proportional brakes 38. The application of the brakes decreases the output of A13, which decreases the output of Q15 and thereby decreases the current through the brakes. This feedback system produces the proportional braking action. The amplified VFB-VT voltage from A12 is also applied to a comparator A14. The output of A14 goes high only if this amplified voltage is greater than 4 volts. The high output of A14 drives a transistor Q16, which turns off a Darlington pair Q17, causing the motor brake to be applied and, along with the proportional brakes, slows down the device. When the velocity of the device decreases to the point where the amplified VFB-VT voltage is less than 4 volts, the output from F14 will fall to zero and Q16 will turn off. The device is then slowed only by the proportional brakes 38 until the velocity signal VFB equals the throttle command signal VT. When the signal VFB equals VT, the output of A13 goes low, releasing the proportional brakes. When the hand grip 120 is brought to the neutral position, the VT signal always goes to zero and the motor brake locks. Therefore, when the device is stopped the motor brake is always engaged, and with power applied, the proportional brakes 38 are also applied because of the braking circuit A10 and Q14.

In conclusion, a power steering and throttle system has been provided for a mobile medical diagnostic device which facilitates safe maneuvering of the device within a hospital by an operator trailing the device. An electrical braking system has also been provided which automatically applies the brakes in proportion to the deceleration of the throttle by the operator.

While a specific embodiment of the present invention has been illustrated and described herein, it is realized that modifications and changes will occur to those skilled in the art. It is, therefore, to be understood that the appended claims are intended to cover all such modifications and changes as fall within the true spirit and scope of the invention.

What is claimed is:

1. An automatic electrical brake system for a mobile medical diagnostic device having a self-propelling motor means and a supporting wheel assembly and a hand operable throttle control, said system comprising:
an electromechanical brake operatively associated with the wheel assembly, said brake being engagable proportionally in response to electrical current applied thereto,
means for sensing the velocity of the device and producing a present velocity signal,
means for sensing the position of the throttle control and producing a throttle command signal,
circuitry means for comparing the present velocity signal to the throttle command signal and, when the velocity signal is greater than the throttle command signal, applying current to said brake proportionally to the difference in the signals, a motor brake operatively associated with the self-propelling motor means, and circuitry means for comparing the present velocity signal to the throttle command signal and, whenever the velocity signal is a preselected amount greater than the throttle command signal, applying current to said motor brake.

2. The brake system as recited in claim 1, wherein said velocity sensing means includes an electromechanical tachometer which has a rotor shaft idler that rides against the wheel of the wheel assembly, and wherein said throttle control sensing means includes a potentiometer having a wiper arm which moves in proportion to the position of the control.

3. The brake system as recited in claim 2 wherein said circuitry means comprises:

a differential amplifier which has a high output when said velocity signal exceeds said command signal, an operational amplifier which receives the output signal from said differential amplifier, and a control means which receives the high signal from said operational amplifier and proportionally applies current to said brakes.

4. A method for automatically braking a mobile medical diagnostic device having a supporting wheel assembly, a self-propelling motor means, a proportional electromechanical brake, a motor brake associated with the self-propelling motor means, and a hand operable throttle control, comprising:

sensing the present velocity of the device and producing a present velocity signal, sensing the position of the throttle and producing a throttle command signal, comparing the present velocity signal to the throttle command signal, applying current to the brake in proportion to the difference in the signals whenever the velocity signal is greater than the throttle command signal, and comparing the present velocity signal to the throttle command signal and, whenever the velocity signal is a preselected amount greater than the throttle command signal, applying current to said motor brake.

5. A control system for a mobile medical diagnostic device having self-propelling means, a steerable wheel assembly and a supporting wheel assembly, comprising:

a handle assembly having a rotatable base with a generally vertical operative axis, a support extending upward from said base, a hand engagable grip extending generally horizontally from said support through the operative axis so that said handle assembly can be rotated about the operative axis in desired left and right directions of travel of the device, means for sensing the position of said handle assembly, means for actuating an electric motor coupled to the steerable wheel assembly to direct the wheel assembly into a position corresponding to said handle assembly, said hand engagable grip being independently rotatable about its longitudinal axis, means for sensing the direction and amount of rotation of said grip and producing a throttle command signal, means for sensing the present velocity of the device and producing a velocity signal, an electromechanical brake operatively associated with the supporting wheel assembly, circuitry means for comparing the throttle command signal with the velocity signal, circuitry means interconnecting the handle assembly with the self-propelling means and with said brake such that if the throttle command signal is greater than the velocity signal, the self-propelling means will produce a higher velocity of the device, and, if the velocity signal is greater than the throttle command signal, the brakes will be actuated proportionately to the difference and produce a lower velocity of the device.

6. The control system as recited in claim 5 and including means for modulating said interconnecting circuitry means in response to the rotational position of said handle assembly about its vertical operative axis.

7. The control system as recited in claim 6 wherein said interconnecting circuitry reduces the throttle command in proportion to the degree in which said handle is rotated from a predetermined central position.

* * * * *